(12) United States Patent
Blumm et al.

(10) Patent No.: US 9,164,049 B2
(45) Date of Patent: Oct. 20, 2015

(54) TEMPERATURE-CONTROL DEVICE FOR THERMOANALYTICAL ANALYSES

(75) Inventors: Juergen Blumm, Selb (DE); Thomas Denner, Selb (DE)

(73) Assignee: Netzsch-Gerätebau GmbH (DE)

( * ) Notice: Subject to any disclaimer, the term of this patent is extended or adjusted under 35 U.S.C. 154(b) by 0 days.

(21) Appl. No.: 13/584,382

(22) Filed: Aug. 13, 2012

(65) Prior Publication Data

US 2012/0307864 A1  Dec. 6, 2012

Related U.S. Application Data

(63) Continuation of application No. PCT/DE2011/000132, filed on Feb. 10, 2011.

(30) Foreign Application Priority Data

Feb. 18, 2010  (DE) .................. 10 2010 008 486

(51) Int. Cl.
| | | |
|---|---|---|
| G01K 1/08 | (2006.01) | |
| G01N 25/22 | (2006.01) | |
| G01N 25/48 | (2006.01) | |
| G01N 5/04 | (2006.01) | |

(52) U.S. Cl.
CPC .............. *G01N 25/4806* (2013.01); *G01N 5/04* (2013.01)

(58) Field of Classification Search
CPC .................................................... G01K 17/04
USPC ................ 374/31–41, 158, E01.011
See application file for complete search history.

(56) References Cited

U.S. PATENT DOCUMENTS

| 4,031,740 | A | | 6/1977 | Achermann | |
|---|---|---|---|---|---|
| 4,208,907 | A | * | 6/1980 | Townsend et al. | 374/34 |
| 4,308,008 | A | * | 12/1981 | Hentze | 432/1 |
| 5,100,244 | A | * | 3/1992 | Kniebes | 374/36 |
| 5,156,459 | A | * | 10/1992 | Baker et al. | 374/32 |
| 5,439,291 | A | | 8/1995 | Reading | |
| 5,509,733 | A | * | 4/1996 | Danley | 374/11 |
| 6,431,747 | B1 | * | 8/2002 | Danley | 374/10 |
| 2002/0024349 | A1 | | 2/2002 | Hirayama et al. | |
| 2003/0086473 | A1 | * | 5/2003 | Popelar et al. | 374/139 |
| 2008/0080591 | A1 | * | 4/2008 | Tanaka et al. | 374/179 |
| 2008/0181281 | A1 | * | 7/2008 | Tanaka | 374/11 |
| 2008/0304542 | A1 | * | 12/2008 | Danley | 374/31 |
| 2009/0052494 | A1 | * | 2/2009 | Wijffels | 374/10 |

FOREIGN PATENT DOCUMENTS

| EP | 0884585 A2 | 12/1998 |
|---|---|---|
| GB | 2204953 A | 11/1988 |

OTHER PUBLICATIONS

International Search Report; Application No. PCT/DE2011/000132; Issued: Jul. 4, 2011; Mailing Date: Jul. 18, 2011; 3 pages.

* cited by examiner

*Primary Examiner* — Lisa Caputo
*Assistant Examiner* — Nasir U Ahmed
(74) *Attorney, Agent, or Firm* — Whitmyer IP Group LLC

(57) ABSTRACT

A temperature-control device for thermoanalytical analyses, including a housing, one heating element, one protective sheath disposed in the housing, wherein the protective sheath is connectable to a gas supply. The heating element is partially arranged inside the protective sheath.

13 Claims, 2 Drawing Sheets

TEMPERATURE-CONTROL DEVICE FOR THERMOANALYTICAL ANALYSES

CROSS-REFERENCE TO RELATED APPLICATIONS

The present invention is a continuation of pending International Patent Application PCT/DE2011/000132 filed on Feb. 10, 2011, which designates the United States and claims priority from German Patent Application 10 2010 008 486.7 filed on Feb. 18, 2010, the content of which is incorporated herein by reference.

FIELD OF THE INVENTION

The present invention relates to a temperature-control device for thermoanalytical analyses, comprising a housing, at least one heating element and at least one protective sheath disposed in the housing, said protective sheath being connectable to a gas supply.

BACKGROUND OF THE INVENTION

Such temperature-control devices are known from the prior art and are used for example in devices for thermal analysis, such as for example a dynamic difference calorimeter, thermal balances and devices for simultaneous thermal analysis. The mentioned devices for thermal analysis are used for material characterisation, i.e. amongst other things for the analysis of polymers and pharmaceutical substances or textiles. With the aforementioned analysis devices, the material samples to be analysed are heated or cooled in a temperature-control device, wherein conventional measured variables are for example the expansion behaviour, weight changes, phase conversion temperatures and enthalpy changes. At present, tube furnaces are used as temperature-control devices in the thermal analysis devices described above, said tube furnaces being equipped with resistance heaters acting as heating elements, wherein the heating elements are disposed outside a protective sheath or the protective tube. In such analyses, however, the tube furnaces known from the prior art come up against their limitations, which presuppose rapid heating of the material sample to be analysed or the atmosphere surrounding the material sample. In other words, these furnaces cannot produce heating rates of several 100 K/min on account of their thermal mass.

Accordingly, it is a problem of the present invention to make available a temperature-control device of the type described at the outset, which enables rapid temperature increases whilst avoiding heat losses and at the same time produces a homogeneous temperature field inside the temperature-control device.

SUMMARY OF THE INVENTION

This problem is solved with a temperature-control device of the type described at the outset, wherein the heating element is disposed at least partially inside the protective sheath.

In contrast with the prior art, the heating element is disposed according to the invention inside the protective sheath or the protective tube in order to be able to heat a material sample to be analysed or the atmosphere inside the protective sheath more quickly. The heating element is preferably disposed inside the protective sheath directly around a material sample to be analysed or a sensor arrangement. Apart from very rapid measurements up to a temperature of 1250° C., very high heating rates at over 1000 K/min can also be achieved with the temperature-control device according to the invention.

Furthermore, conventional sample holders and sensor arrangements can be used with the temperature-control device according to the invention. Accordingly, special sample carriers or sensor arrangements designed for the temperature-control device are not required.

According to a preferred embodiment of the invention, provision is made such that the protective sheath is a protective tube produced from ceramic or glass.

In this connection, a further preferred embodiment of the invention makes provision such that the protective tube is provided with a reflecting, metallic coating on its outer surface facing the housing. The thermal radiation is repeatedly reflected by the reflecting, metallic coating, as a result of which the temperature field inside the heating element is homogenised. A sample to be analysed can thus be heated uniformly. Furthermore, thermal radiation losses outwards in the direction of the housing can be minimised by the coating, as a result of which excessive heating of the housing or of the furnace casing is also reduced. Accordingly, the heat output generated by the heating element for the most part remains inside the protective tube produced from glass or ceramic and accordingly also in the region of the sample to be analysed.

According to the invention, the heating element is produced at least partially from metal or ceramic. A heating element produced from metal or ceramic usually exhibits a very high resistance to thermal shocks at the same time as a low thermal capacity. In other words, heating processes with high temperatures and also cooling processes can be carried out alternately at short intervals after one another using a metallic or ceramic heating element, without the heating element becoming adversely affected or even damaged, for example due to stresses in the material.

In order to protect the user of a temperature-control device according to the invention and also the reflecting metallic protective tube coating, provision is made according to a development of the invention such that the protective tube can be cooled by means of air cooling, air being fed continuously to the protective tube. Relatively low temperatures of the protective tube and also of the housing are thus achieved, wherein precisely a low temperature of the housing markedly reduces the risk of injury to a user due to being burnt on the housing.

According to the invention, the temperature-control device can produce heating rates in the range from 0 K/min to over 1000 K/min.

In order to prevent thermal radiation in the direction of the analysis device with which the temperature-control device is connected, a development of the invention makes provision such that the temperature-control device comprises at least one radiation protection shield disposed at least partially in the protective sheath. The radiation protection shield in the protective sheath is preferably disposed in a region beneath the heating element.

In order to position a material sample to be analysed in the temperature-control device, the temperature-control device comprises according to the invention at least one sample carrier disposed at least partially in the protective sheath. The sample carrier is preferably positioned in the protective sheath in such a way that the material sample to be analysed is surrounded by the heating element in the protective sheath, in order to allow the material sample to be heated uniformly, i.e. to surround the material sample with a homogeneous temperature field. Furthermore, temperatures of up to 1250° C. for corresponding analyses of a material sample can be reached very quickly by means of the arrangement of the heating element directly around the sample carrier.

According to a preferred embodiment of the invention, the temperature-control device can comprise at least one sensor arrangement disposed at least partially in the protective sheath. The sensor arrangement is directly surrounded by the heating element through the inventive arrangement of the heating element in the protective sheath, as a result of which homogeneous heating is guaranteed in the region of the sensor arrangement and the sample carrier inside the temperature-control device.

Furthermore, the present invention relates to an analysis device with a temperature-control device of the type described above.

According to a preferred embodiment of the invention, the temperature-control device is fitted to the analysis device in a removable or replaceable manner. In other words, the temperature-control device forms a self-enclosed unit of an analysis device, as a result of which the temperature-control device can be connected to different analysis devices.

According to a preferred embodiment, the analysis device is vacuum-tight, as a result of which analyses of a material sample under vacuum conditions are enabled.

According to the invention, the analysis device can be, amongst other things, an analysis device for gas analysis, a thermal balance or a thermal analysis device.

BRIEF DESCRIPTION OF THE DRAWINGS

The invention is explained below by way of example with the aid of appended FIG. 1-2. In the figures.

DETAILED DESCRIPTION OF THE INVENTION

Figure 1:
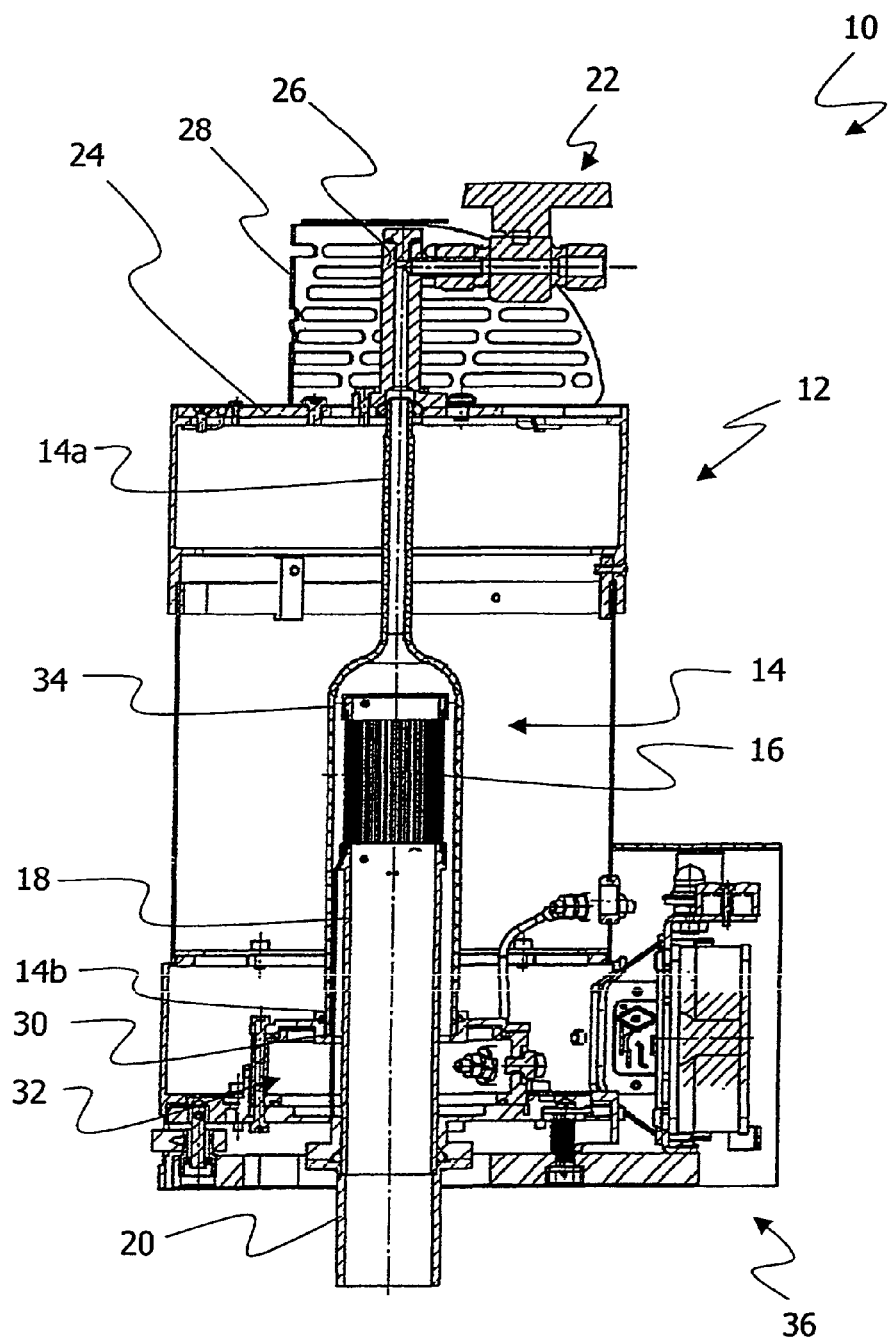
FIG. 1 shows a cross-sectional view of the temperature-control device according to the invention.

FIG. 1 shows a cross-sectional view of the temperature-control device according to the invention, which is denoted generally by 10.

Temperature-control device 10 comprises a housing 12, in which protective sheath 14 is disposed. An essentially tubular heating element 16 made of metal or ceramic is disposed in protective sheath 14. Heating element 16 can also consist of a plurality of individual heating bodies. Heating element 16 is positioned inside protective sheath 14 or the protective tube via a tube section 18 in a predetermined position inside protective tube 14. The position of heating element 16 is selected such that, in the state of temperature-control device 10 fitted to an analysis device (not shown), it directly surrounds a sample carrier (not shown here) with a material sample located thereon or a sensor arrangement (not shown here) (FIG. 2) and enables homogeneous heating with very high heating rates of over 1000 K/min.

Tube section 18 of temperature-control device 10 is open to the bottom according to FIG. 1 so that, when temperature-control device 10 is fitted to a thermal analysis device (not shown), a sample carrier or a sensor arrangement (FIG. 2) can be pushed via tube section 18 into protective tube 14 and into heating element 16.

Furthermore, there is connected to tube section 18 a connection pipe 20, with which temperature-control device 10 can be connected to an analysis device. In other words, gas or pressure sources can be connected to connection pipe 20 in order to produce predetermined atmospheric conditions or a vacuum in protective tube 14. If a specific gas is used for the analysis of a material sample, the gas can then be carried away via a gas outlet valve 22 in the upper region of housing 12 of temperature-control device 10.

In this connection, it can be seen in FIG. 1 that protective tube 14 runs bell-shaped in a region above heating element 16 and thus reduces its diameter. In other words, protective tube 14 above heating element 16 transforms into a section 14a with a very much smaller diameter. With section 14a having the smaller diameter, protective tube 14 is connected at an upper wall 24 of the housing to a tube section 26, to which gas outlet valve 22 is fitted. Gas outlet valve 22 is also fixed to a sheet metal body 28 beside tube section 26 in order to guarantee a reliable operation, i.e. the discharge of the gas and the shutting-off of gas outlet valve 22.

In its end 14b lying opposite section 14a with a reduced diameter, protective tube 14 is supported on a disc-shaped wall section 30. Wall section 30 is followed by space 32, which is connected atmospherically to protective tube 14. Via space 32, protective tube 14 can be supplied with a predetermined gas and can be subjected to pressure.

Provided on protective tube 14, at its outer side 34 facing housing 12, is a reflecting coating (not represented), which prevents thermal radiation in the direction of housing 12 and ensures a homogeneous temperature field inside protective tube 14 and in particular in the region of heating element 16. On account of the reflecting coating of protective tube 14, an accompanying factor is that housing 12 is prevented from becoming intensely heated, as a result of which, apart from improved homogeneity of the temperature field in protective tube 14, the risk of injury to a user due to being burnt on housing 12 is reduced.

Various peripheral parts of temperature-control device 10 are denoted generally by 36 in FIG. 1. The assembly parts for the connection between the temperature-control device and the analysis device, electrical connections between the temperature-control device and analysis devices and devices for cooling protective tube 14 are accommodated here.

Figure 2:
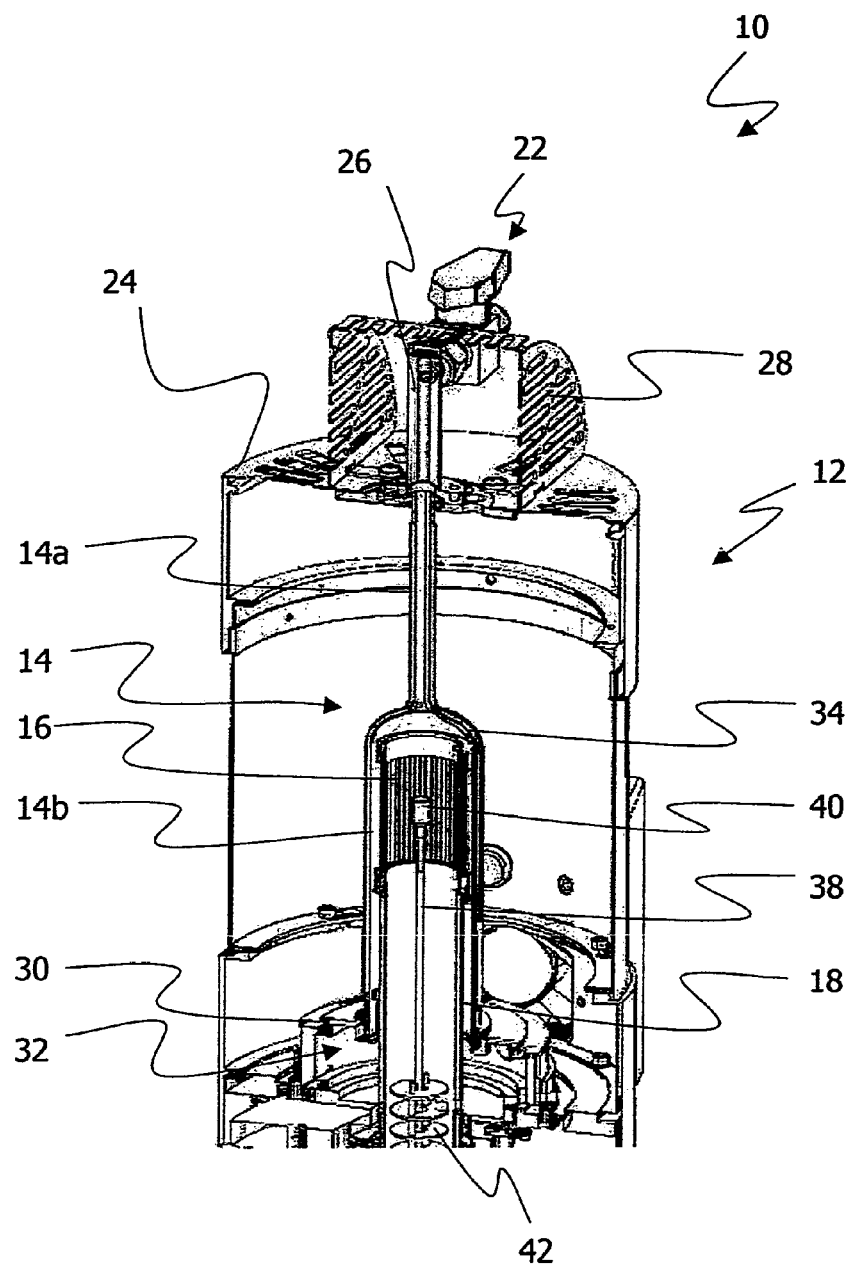
FIG. 2 shows a perspective view of the temperature-control device according to the invention.

FIG. 2 shows a perspective view of temperature-control device 10 according to FIG. 1 with a sample carrier 38 inserted into tube section 18 and into protective tube 14.

As can be seen from FIG. 2, by means of sample carrier 38, a material sample located on a carrier section 40 of sample carrier 38 is placed centrally in heating element 16. In other words, heating element 16 surrounds carrier section 40, as a result of which homogeneous heating of a sample with very high heating rates is achieved.

Carrier section 40 of sample carrier 38 can be provided with differently designed sample-carrier or sensor arrangements, which can be adapted in each case to the material sample to be analysed.

Together with sample carrier 38, a radiation shield 42 is inserted into tube section 18 of temperature-control device 10 in order to prevent thermal radiation in the direction of the analysis device (not shown here) located beneath temperature-control device 10 and at the same time to guarantee as homogeneous a temperature field as possible in protective tube 14.

What is claimed is:

1. A temperature-control device for thermoanalytical analyses, comprising
  a housing,
  at least one protective sheath disposed in the housing, the protective sheath being connectable to a gas supply in order to adjust an atmospheric condition or vacuum in the protective sheath,
  at least one heating element generating heat, wherein the heating element is disposed at least partially inside the protective sheath, the protective sheath providing thermal protection for the housing against the heat generated within the protective sheath, and at least one movable sample carrier configured to hold a material sample, the sample carrier being disposed directly adjacent to the heating element for thermoanalytical analysis of the material sample;

wherein the heating element comprises at least one or metal or ceramic.

2. The temperature-control device according to claim 1, wherein the protective sheath is a protective tube produced from ceramic or glass.

3. The temperature-control device according to claim 1, wherein the protective sheath includes a metallic coating on its outer surface facing the housing, the coating being adapted to reflect thermal radiation.

4. The temperature-control device according to claim 1, wherein the protective sheath can be cooled by means of air cooling, air being fed continuously to the protective sheath.

5. The temperature-control device according to claim 1, wherein the temperature-control device produces heating rates in a range from 0 K/min to over 1000 k/min.

6. The temperature-control device according to claim 1, further comprising at least one radiation protection shield disposed at least partially in the protective sheath, the radiation protection shield blocking transmission of thermal radiation from the heating element to an analysis device that is adapted to connect to the temperature-control device.

7. The temperature-control device according to claim 1, wherein the sample carrier is movably disposed at least partially in the protective sheath, the sample carrier being movable into the protective sheath to position the material sample so that the material sample is surrounded by the heating element.

8. The temperature-control device according to claim 1, further comprising at least one sensor arrangement disposed at least partially in the protective sheath and surrounded by the heating element.

9. An analysis device comprising a connection for connecting with the temperature-control device according to claim 1.

10. The analysis device according to claim 9, wherein the temperature-control device is removably connected to the analysis device.

11. The analysis device according to claim 9, wherein the analysis device is vacuum-tight.

12. The analysis device according to claim 9, wherein the analysis device provides gas analysis.

13. The analysis device according to claim 9, wherein the analysis device is a thermal balance or a thermal analysis device.

* * * * *